(12) United States Patent
Nishiumi et al.

(10) Patent No.: US 7,465,923 B2
(45) Date of Patent: Dec. 16, 2008

(54) TESTING METHOD FOR SEMICONDUCTOR DEVICE, TESTING APPARATUS THEREFOR, AND SEMICONDUCTOR DEVICE SUITABLE FOR THE TEST

(75) Inventors: Toshiya Nishiumi, Kawasaki (JP); Koki Ando, Kuwana (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 11/654,663

(22) Filed: Jan. 18, 2007

(65) Prior Publication Data

US 2007/0114410 A1 May 24, 2007

Related U.S. Application Data

(63) Continuation of application No. PCT/JP2004/010485, filed on Jul. 23, 2004.

(51) Int. Cl.
*G01N 23/00* (2006.01)
(52) U.S. Cl. .................. 250/311; 250/306; 250/307
(58) Field of Classification Search .................. 250/311
See application file for complete search history.

(56) References Cited

U.S. PATENT DOCUMENTS 6,531,697 B1 * 3/2003 Nakamura et al. .......... 250/311

2004/0158409 A1 * 8/2004 Teshima et al. ............... 702/22

FOREIGN PATENT DOCUMENTS

| JP | 61-110954 | 5/1986 |
| JP | 5-217536 | 8/1993 |
| JP | 6-139988 | 5/1994 |
| JP | 8-5528 | 1/1996 |
| JP | 2003-14667 | 1/2003 |
| JP | 2004-22318 | 1/2004 |

* cited by examiner

*Primary Examiner*—Jack I. Berman
*Assistant Examiner*—Andrew Smyth
(74) *Attorney, Agent, or Firm*—Kratz, Quintos & Hanson, LLP

(57) ABSTRACT

The present invention relates to a method of testing, in the manufacturing process of an LSI (large scale integration) device, a result apparatus therefor, and a cross-sectional microstructure of the LSI device. The method includes thinning a semiconductor chip such that the semiconductor chip includes a substrate crystal and a portion added by the manufacturing process, irradiating an electron beam to the semiconductor chip, detecting an electron beam transmitted through the semiconductor chip to thereby obtain an electron beam diffraction image, removing an electron beam diffracted due to the substrate crystal, and comparing, in the electron beam diffraction image, the thickness of grating stripes obtained from the substrate crystal with the thickness of the portion added by the manufacturing process.

6 Claims, 15 Drawing Sheets

US 7,465,923 B2

TESTING METHOD FOR SEMICONDUCTOR DEVICE, TESTING APPARATUS THEREFOR, AND SEMICONDUCTOR DEVICE SUITABLE FOR THE TEST

This application is a continuation of international application PCT/JP04/010485 filed Jul. 23, 2004.

TECHNICAL FIELD

The present invention relates to a method of testing, in the manufacturing process of an LSI (large scale integration) device, a result obtained by the manufacturing process, a testing apparatus therefor, and a semiconductor device suitable for the test. The present invention relates, in particular, to a testing method used to immediately and accurately perform a test of the cross-sectional microstructure of an LSI device obtained by the manufacturing process, a testing apparatus therefor, and a semiconductor device suitable for the test.

BACKGROUND ART

As the micronization of an LSI (large scale integration) device progresses, accurate measurement of a resultant product obtained by the manufacturing process becomes necessary. This is because an accurate result in accordance with the degree of micronization is demanded in the manufacturing process, and the determination therefor requires the accurate measurement. It is also because the result of the above accurate measurement is used in the feedback for the accuracy of the manufacturing process, the management of the manufacturing process, or the management of the performance of the LSI device obtained by the manufacturing process, for example. In the manufacturing process, therefore, the measurement of the result obtained by the manufacturing process is necessary, and the measurement requires accuracy. However, while the measurement relating to the planar structure of the LSI device (e.g., the length measurement of the width of a photoresist) is usually performed immediately, the measurement relating to the cross-sectional structure, such as the length measurement of a gate oxide film in the growth process thereof, the length measurement of a shallow trench isolation film in the growth process thereof, and the length measurement of a diffusion preventing film for preventing the diffusion of a metal from a metal wiring in the growth process thereof, for example, has not been performed to measure the result of the manufacturing process immediately and accurately in the manufacturing process.

Meanwhile, as means for observing the cross-sectional microstructure, a TEM (Transmission Electron microscope) apparatus is usually used which includes a unit for irradiating an electron beam, an electron lens used to guide electrons transmitted through a sample or electrons scattered by the sample to a detector, a diaphragm for adjusting the amount of the electron beam, and a transmitted electron detection unit for detecting the transmitted electron beam.

In the observation of the sample by the above TEM apparatus, the amount of electrons to be guided to the transmitted electron detection unit has been determined by the electron lens, with the opening of the diaphragm fixed.

In the TEM apparatus according to the conventional example 1, however, the structure of a semiconductor detector which serves also as the diaphragm for the transmitted electron detector is designed to be the structure of a diaphragm/semiconductor detector illustrated in FIG. 1, to thereby make the opening of the diaphragm/semiconductor detector variable and thus limit the passage of unintended scatted electrons from the diaphragm/semiconductor detector. Accordingly, improvement is observed in an electron diffraction image obtained by the TEM apparatus after the transmission of electrons through the sample (Patent Document 1: Japanese Unexamined Patent Application Publication No. 6-139988).

The diaphragm/semiconductor detector illustrated in FIG. 1 includes a semiconductor detector 1, a fixing pin 2, a lever pin 4, a guide hole 3, a rotary ring 5, a board 6, and a shaft 7. When the rotary ring 5 is rotated by the shaft 7, the semiconductor detector 1 moves along the guide hole 3 and rotates around the fixing pin 2. As a result, the diameter of a central hole formed by a plurality of the semiconductor detectors 1 changes. Thereby, the amount of electrons directed to a transmitted electron detector placed behind the semiconductor detectors 1 is adjusted. Accordingly, with the transmitted electron detector and the semiconductor detector 1, a dark-field or bright-field electron diffraction image in accordance with the amounts of electrons captured by the respective detectors can be obtained.

Meanwhile, in a TEM apparatus according to the second conventional example 2, a diaphragm for a transmission detector has an opening of a plurality of sizes, and thus the amount of electrons passing through the diaphragm can be adjusted. As a result, improvement is observed in an electron diffraction image obtained by the TEM apparatus after the transmission of electrons through a sample (Patent Document 2: Japanese Unexamined Patent Application Publication No. 5-217536).

The diaphragm of the TEM apparatus according to the conventional example 2 is herein illustrated in FIG. 2. The diaphragm of FIG. 2 includes a lower diaphragm plate 133 having a plurality of opening sets each including openings of four sizes, an upper diaphragm plate 130 having one of the above opening sets, a lower retaining mechanism 134 for the lower diaphragm plate 133, an upper retaining mechanism 131 for the upper diaphragm plate 130, lower diaphragm holes 136 included in the lower diaphragm plate 133, and upper diaphragm holes 132 included in the upper diaphragm plate 130. Thus, the amount of electrons of an electron beam 135 can be adjusted by the upper diaphragm plate 130 and then further by the lower diaphragm plate 133. Furthermore, the electron beam 135 can be further narrowed to an arbitrary amount by slightly displacing the upper diaphragm plate 130 and the lower diaphragm plate 133 from each other.

The above apparatus, however, has not been used in the manufacturing process as means for immediately and accurately measuring the result obtained by the manufacturing process.

Patent Document 1: Japanese Unexamined Patent Application Publication No. 6-139988
Patent Document 2: Japanese Unexamined Patent Application Publication No. 5-217536

DISCLOSURE OF INVENTION

Problem to be Solved by the Invention

A method of immediately and accurately measuring, in the manufacturing process of a semiconductor device, a result of the manufacturing process in terms of the cross-sectional structure, a measuring apparatus therefor, and a semiconductor device suitable for the measurement are provided.

Means to Solve the Problem

To solve the above problem, the invention provides a measuring method characterized by including a sample production step of producing a sample by thinning an object including a crystal portion; a step of irradiating an electron beam to the sample and narrowing, to an arbitrary amount, an electron beam which is included in a transmitted electron-beam transmitted through the sample and which is diffracted by the crystal portion, to thereby obtain electron beam imaging from the transmitted electron beam; and a step of comparing, in the electron beam imaging, the width of grating stripes obtained from the crystal portion with the width of an arbitrary portion.

According to the measuring method of the invention, in the electron beam imaging obtained by irradiating the electron beam to the sample, the grating stripes obtained from the crystal portion in the sample are made clear, without strict control of the thickness of the sample and the like. Thus, there is an effect of enabling the length measurement of the width of an arbitrary portion of a semiconductor device including a semiconductor crystal substrate, such as a result obtained by the manufacturing process of the semiconductor device (e.g., the thickness of a gate oxide film), for example, on the basis of the interval between the above grating stripes.

To solve the above problem, the invention provides a measuring apparatus characterized by including an FIB (focused ion beam) irradiation device for irradiating an FIB to a sample from one angle, an electron beam irradiation device for irradiating an electron beam to the sample from another angle, an electron beam detecting device for detecting the electron beam transmitted through the sample, and an electron beam diaphragm provided between the electron beam detection device and the sample and capable of adjusting the size of an opening through which the electron beam passes.

According to the measuring apparatus of the invention, the above electron beam diaphragm is provided. Thus, there is an effect of being most suitably for implementing the measuring method according to the first invention. Further, since the FIB irradiation device and the electron beam irradiation device are integrated in one device, the result of observation by the TEM apparatus is obtained immediately after the production of the sample by the irradiation of the FIB. Accordingly, there is an effect of reducing the trial and error period taken for the production of the sample.

To solve the above problem, the invention provides a semiconductor device including a circuit element for forming a semiconductor circuit, a measurement element used in a measurement, and a cutting region for separating the semiconductor device. The semiconductor device is characterized by being formed on a semiconductor substrate, and characterized in that the circuit element and the measurement element are the same in the cross-sectional structure, that the measurement element is provided in the cutting region at a position where the measurement element is cut when the semiconductor device is cut into the individual piece from the semiconductor substrate, and that a cut surface of the measurement element is used in the measurement.

According to the semiconductor device of the invention, when the semiconductor device is cut into the individual piece, the cross section of the measurement element is observable. Thus, the semiconductor device is suitable for implementing the measuring method according to the first invention. Further, since the above measurement element is located at an edge of the semiconductor device, there is an effect of enabling easy length measurement with the use of the measuring apparatus of the embodiment example 2. Furthermore, since the above measurement element and the above circuit element are the same in structure, there is an effect of enabling the length measurement of the result of the manufacturing process to be performed immediately and accurately in the manufacturing process, without destroying the above circuit element.

BEST MODE FOR CARRYING OUT THE INVENTION

Embodiment 1 for Carrying Out the Invention (Testing Method)

As an example of measurement to immediately and accurately grasp the result obtained by the manufacturing process of an LSI device, there is a measurement to measure the length of the microstructure of the LSI device.

However, while the length measurement relating to the planar structure of the LSI device (e.g., the length measurement of the width of a photoresist) is usually performed, the length measurement relating to the cross-sectional structure, such as the length measurement of a gate oxide film in the growth process thereof, the length measurement of a shallow trench isolation film in the growth process thereof, and the length measurement of a diffusion preventing film for preventing the diffusion of a metal from a metal wiring in the growth process thereof, for example, involves the following problems and thus has not been easy.

The first problem is that, even through magnified observation using a usual electron microscope or the like, the object of length measurement, i.e., the cross-sectional structure is extremely microscopic (for example, the cross-sectional structure of the gate oxide film is approximately 0.5 nm) and thus has not been easily observed. Meanwhile, in the case of using a TEM apparatus, there is no problem in terms of the resolution, but there are such problems as the contribution of unintended scattered electrons to imaging. Therefore, it has not been easy to obtain an optimal contrast, taking time in such preparations as a sample production operation for removing the unintended scattered electrons (e.g., an operation of adjusting, in accordance with the condition of the apparatus, the thickness of the sample, the size of the sample, and the like which affect the scattering of electrons) and the adjustment of the apparatus prior to the observation of the sample.

Figure 1:
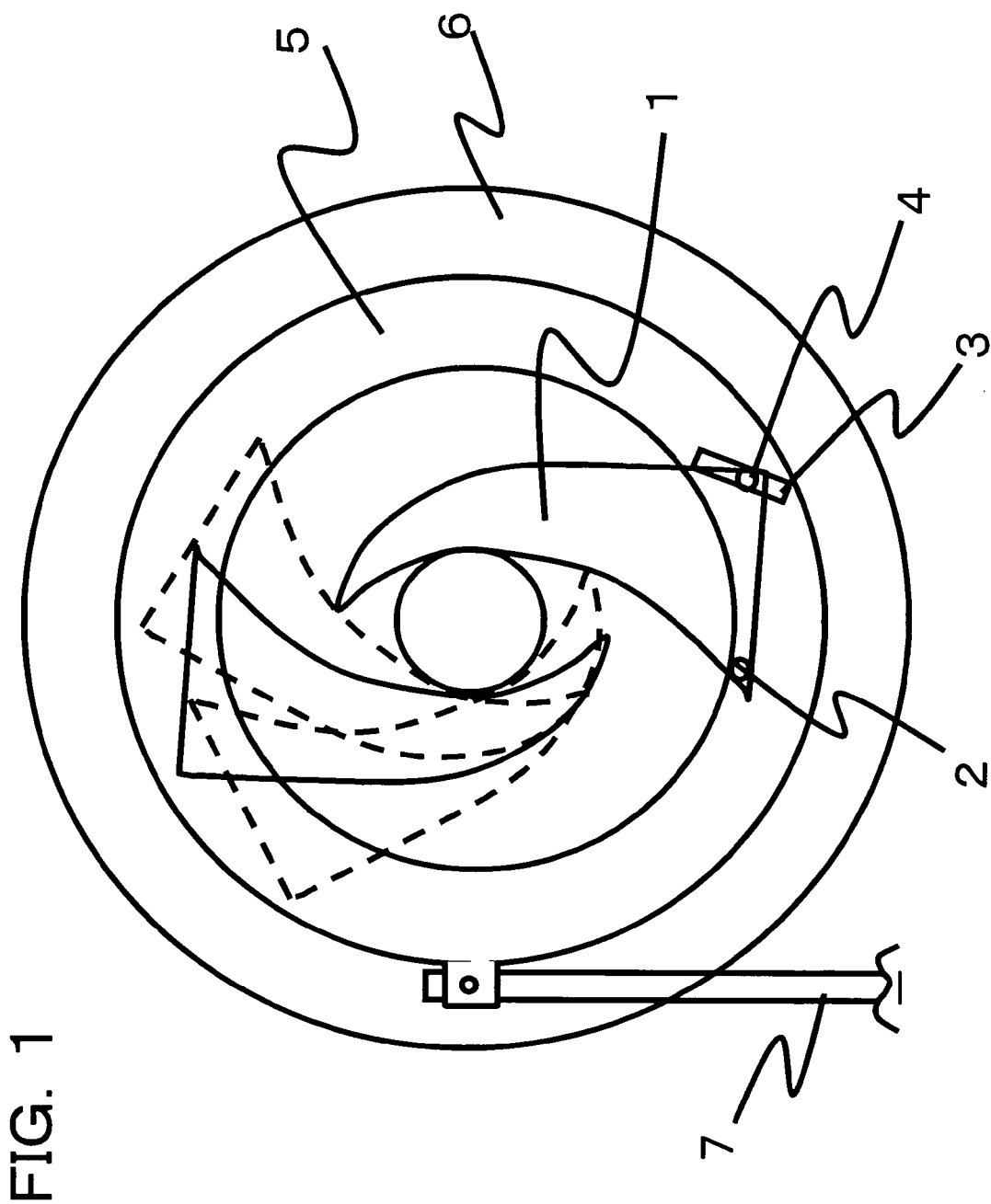
FIG. 1 is a diagram illustrating a diaphragm for an electron beam provided in a TEM apparatus according to the conventional example 1.
Figure 2:
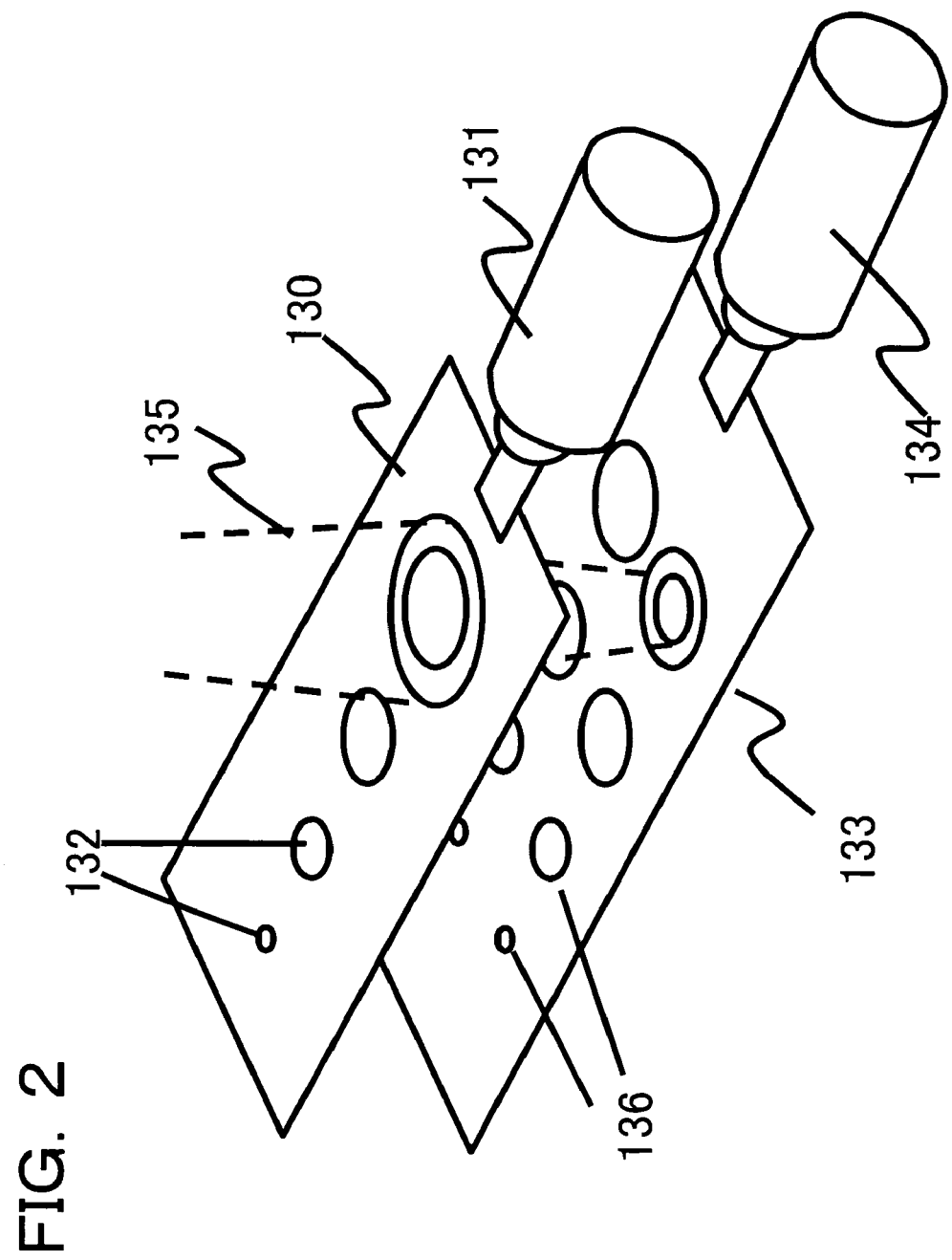
FIG. 2 is a diagram illustrating a diaphragm for an electron beam provided in a TEM apparatus according to the conventional example 2.
Figure 3:
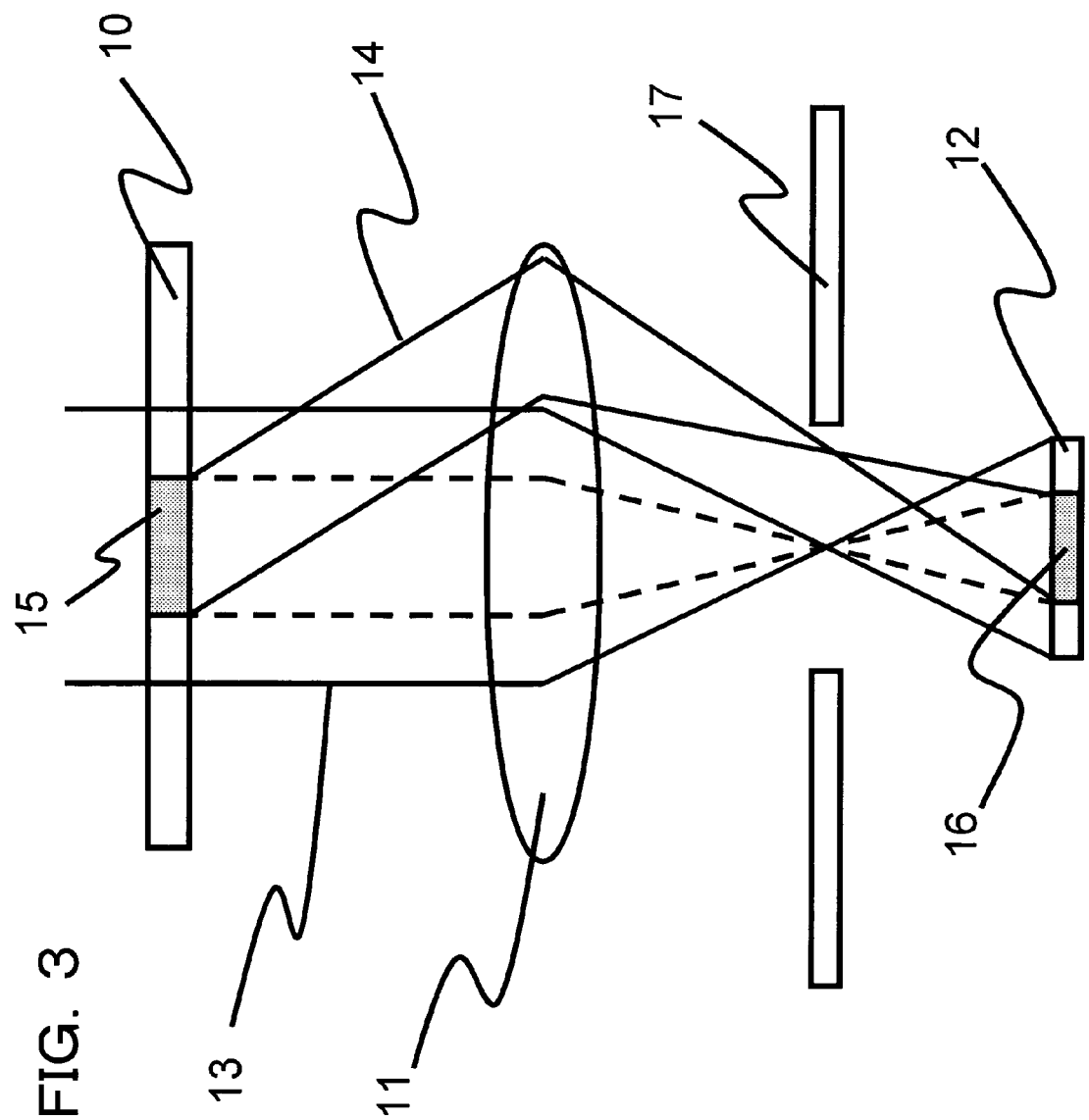
FIG. 3 is a diagram illustrating a state in which an electron beam 13 transmitted through a sample 10 and a scattered electron beam 14 form an electron diffraction image 12.

FIG. 3 shown here is a diagram illustrating a state in which an electron beam 13 transmitted through a sample 10 and a scattered electron beam 14 form an electron diffraction image 12. That is, the sample 10 includes a crystal portion 15, and when an electron beam is irradiated to the sample, the transmitted electron beam 13 hardly scatted by the sample and the scattered electron beam 14 are generated. When both of the transmitted electron beam 13 and the scattered electron beam 14 pass through an electron lens 11, the beams converge. As a result, both of the unscattered and transmitted electron beam 13 and the scattered electron beam 14 pass through a diaphragm 17. Then, a detector detects the electron beams, to thereby form the electron diffraction image 12 including an image 16 which corresponds to the crystal portion 15 of the sample 10.

The second problem is as follows. To perform the length measurement, high accuracy is required in the determination of the length. However, it has not been easy to calculate the accurate length of an observed object from an observed image, unless the viewpoint for observing the cross-sectional structure faces oppositely to an object of length measurement. For example, when a and b represent the accurate length of the observed object and the length in the observed image, respectively, and when it is assumed that the observation is made from a direction inclined by X degrees from the normal line of the observed object, a is the result obtained by dividing b by cosX. However, the direction of the viewpoint cannot be accurately determined solely from the observed image, and thus the accurate length a of the observed object cannot be calculated.

Figure 6:
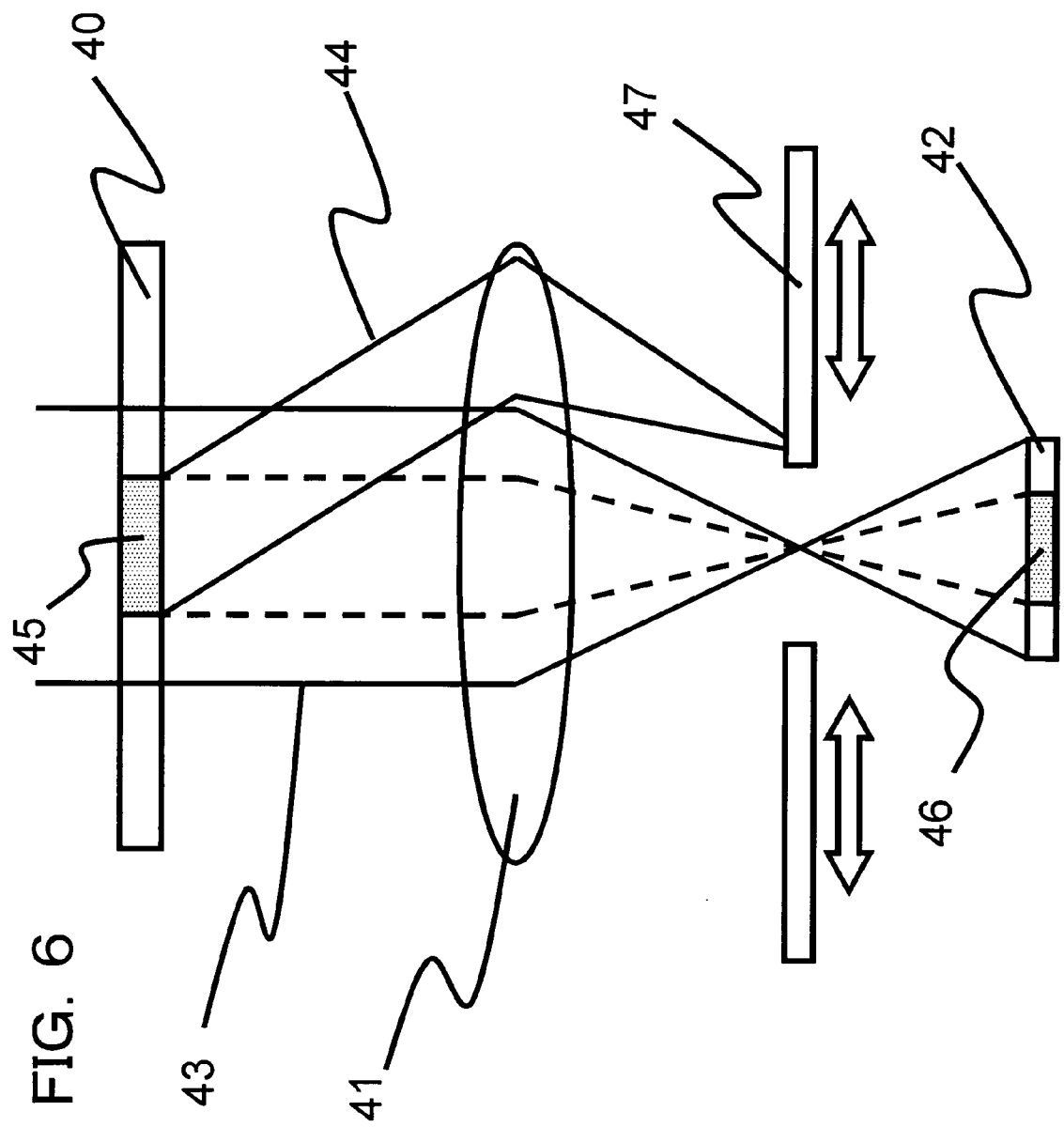
FIG. 6 is a diagram illustrating an image clarification step for clarifying an image by removing an unnecessary electron beam in the testing method according to the embodiment example 1.
Figure 7:
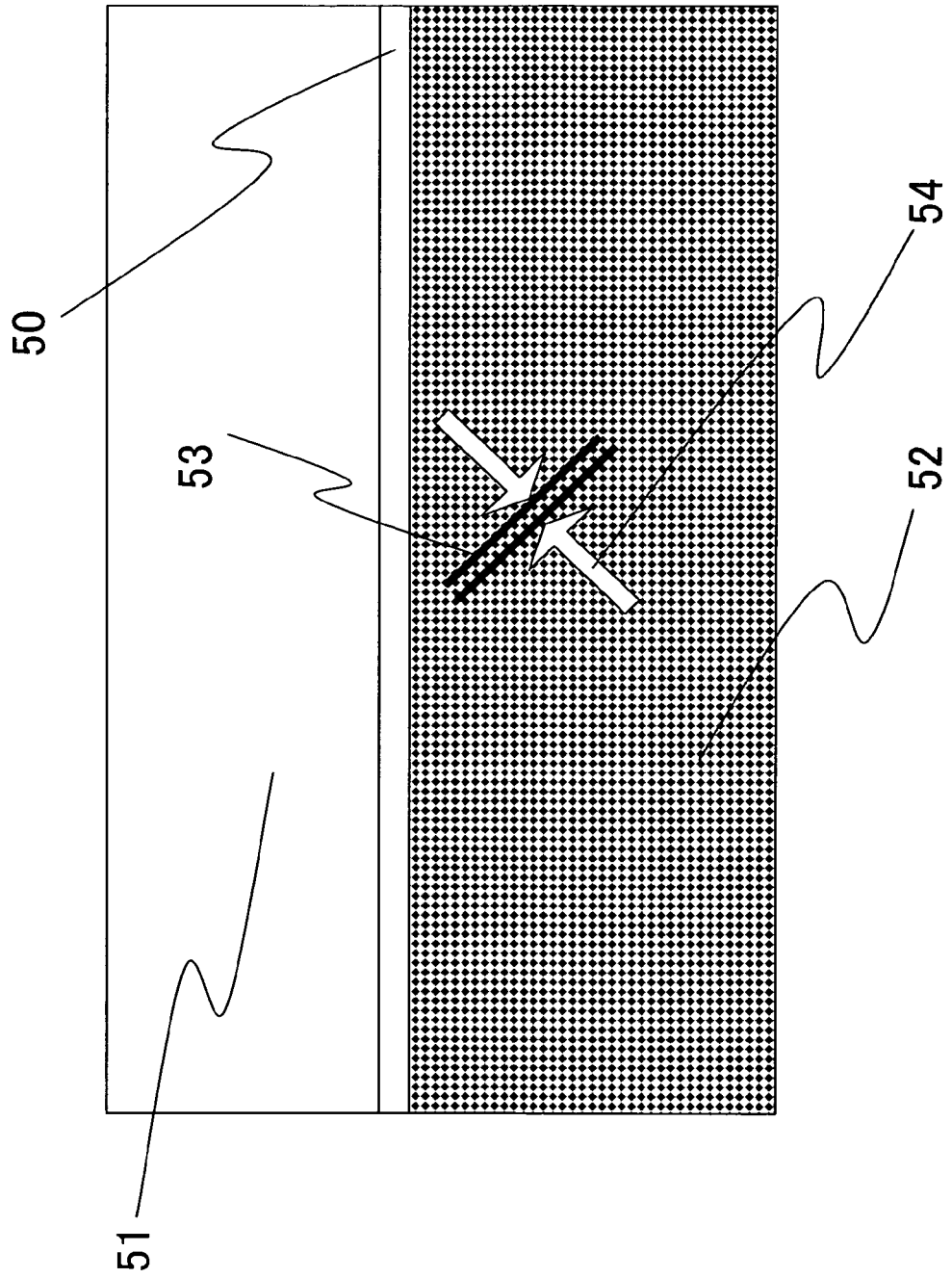
FIG. 7 illustrates a step of comparing the interval between grating stripes obtained from a crystal grating with the thickness of a portion added by the manufacturing process in the testing method according to the embodiment example 1.

Accordingly, a measuring method according to the embodiment example 1 to solve the above problems will be described. To describe the measuring method of the embodiment example 1, FIGS. 4 to 7 will be used, wherein FIG. 4 shows a flowchart, FIG. 5 illustrates a sample production step, FIG. 6 illustrates an image clarification step of obtaining a clear electron diffraction image by irradiating electrons to a sample and narrowing an electron beam transmitted through the sample to an arbitrary amount, i.e., removing an unnecessary electron beam, and FIG. 7 illustrates a length measurement step.

Figure 4:
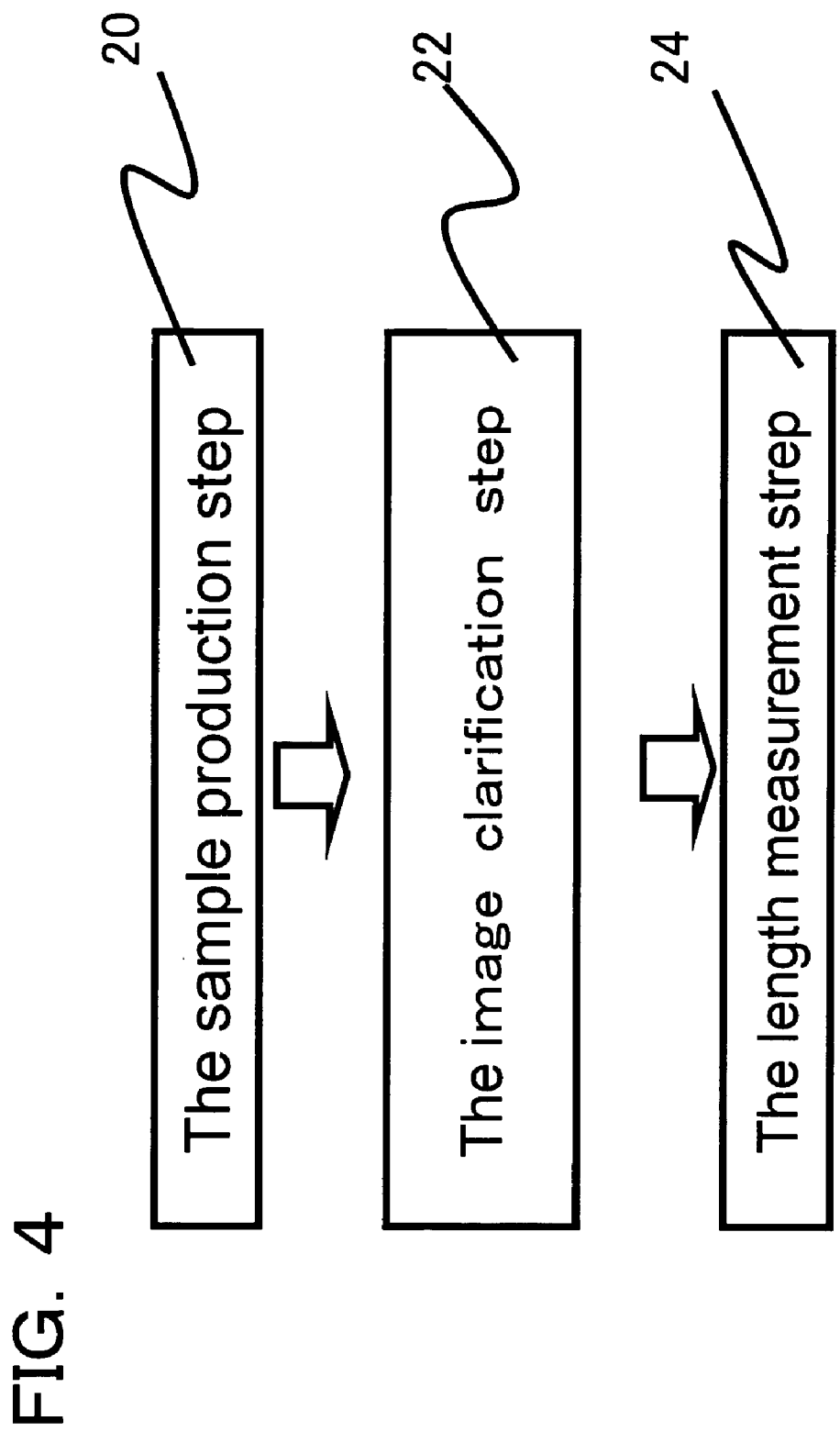
FIG. 4 is a diagram showing a flowchart of a testing method according to the embodiment example 1.

Firstly, FIG. 4 shows the flowchart of the measuring method according to the embodiment example 1, and illustrates that the measuring method according to the embodiment example 1 includes: a sample production step 20 of producing a sample by extracting and thinning a portion desired to be measured, i.e., an observed object; an image clarification step 22 of obtaining a clear electron diffraction image by irradiating electrons to the sample and narrowing an electron beam transmitted through the sample to an arbitrary amount, i.e., removing an unnecessary electron beam; and a length measurement step 24 of comparing, in the electron diffraction image, the width of grating stripes in a portion corresponding to the crystal portion of the sample with the width of a portion added by the manufacturing process, to thereby determine the actual thickness of the above portion added by the manufacturing process.

Figure 5:
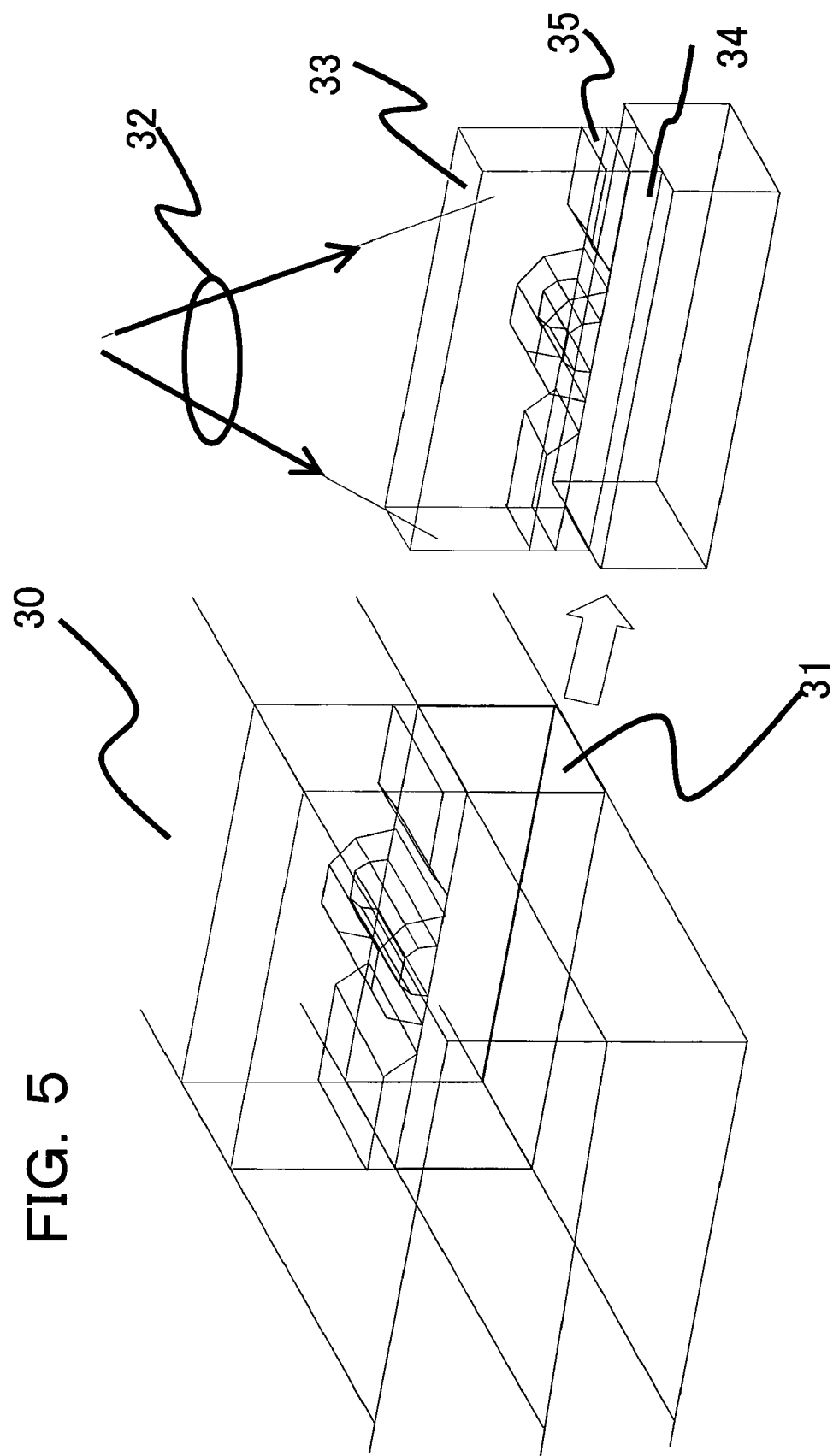
FIG. 5 is a diagram illustrating a sample production step of thinning a sample in the testing method according to the embodiment example 1.

Then, FIG. 5 illustrates the sample production step 20 of thinning the observed object. FIG. 5 includes a left diagram illustrating an observed object 31 in a semiconductor chip 30, and a right diagram illustrating the process of thinning the observed object 31.

In the above sample production step 20, the observed object 31 in the semiconductor chip 30 is first cut out from the semiconductor chip 30, as indicated by an arrow. Then, an FIB 32 is irradiated from the above, and the observed object 31 is trimmed and thinned such that a crystal substrate 34 and a portion 35 added in the manufacturing process appear on the same cross section. Thereby, a sample 33 is produced. The above is the sample production step 22.

As for the thinning, the example of the thinning by irradiating the FIB 32 from the above has been described in the above. However, the thinning may be performed by such means as polishing the observed object 31.

Then, FIG. 6 illustrates the image clarification step 22 for clarifying an image by removing an unnecessary electron beam. As illustrated in FIG. 6, when an electron beam is first applied to a sample 40 including a crystal portion 45, a hardly-diffracted transmitted electron beam 43 and a diffracted transmitted electron beam 44 are generated, and an electron diffraction image 42 including an image 46 of the crystal portion can be obtained on a detector by an electron lens 41. Then, by moving a diaphragm 47 from side to side, as indicated by arrows, the adjustment of the amount of the passing electron beam, i.e., the determination of whether or not to allow the passage of the diffracted transmitted electron beam 44 can be made. In other words, the image clarification step is the step of clarifying the grating stripes formed by a crystal grating in the image 46 of the crystal portion 45 by excluding the passage of the unnecessary diffracted transmitted electron beam 44.

Then, FIG. 7 illustrates the length measurement step 24 including an operation of comparing, on the electron diffraction image, the interval between the grating stripes formed by the crystal grating with the width of the portion added by the manufacturing process. As a result of the image clarification step illustrated in FIG. 6, through which the transmitted electron beam 44 diffracted by the crystal grating has been removed, the crystal grating stripes are made clear in an image 52 of the crystal portion in the electron beam diffraction image. Then, on the electron diffraction image, the length measurement is performed on the interval between the grating stripes indicated by solid lines 53, i.e., the width indicated by white arrows 54, and the width is compared with the width of a portion 50 on the electron diffraction image added by the manufacturing process, to thereby obtain a ratio between them. Accordingly, the actual thickness of the portion added by the manufacturing process, such as the actual thickness of a gate oxide film 50 or an interlayer insulation film 51, is calculated from the actual crystal grating constant and the above ratio. The step described above is the length measurement step 24 for determining the thickness of the portion added by the manufacturing process.

To briefly summarize the above, the measuring method of the embodiment example 1 includes: a sample production step of producing a sample by thinning an observed object from a semiconductor chip such that the observed object includes a substrate crystal and a portion added by the manufacturing process; a step of irradiating an electron beam to the sample and narrowing, to an arbitrary amount, an electron beam which is included in an electron beam transmitted through the sample and which is diffracted by the crystal portion, to thereby obtain an electron beam diffraction image from a detector; and a step of comparing, in the electron diffraction image, the width of grating stripes obtained from the substrate crystal with the width of the portion added by the manufacturing process. Further, the measuring method includes a length measurement step of determining the actual thickness of the portion added by the manufacturing process. Thus, according to the measuring method of the embodiment example 1, it is possible to obtain the electron beam diffraction image in which the grating stripes obtained from the substrate crystal are made clear, by narrowing the electron beam diffracted by the crystal portion, with no strict control of the thickness of the sample or the like. Therefore, there is an effect of enabling the length measurement of the result obtained by the manufacturing process (e.g., the thickness of the gate oxide film) on the basis of the interval between the grating stripes of the substrate crystal in the electron beam diffraction image. Further, since the length measurement is performed on the basis of the interval between the grating stripes obtained from the substrate crystal, there is an effect of not requiring the direction of observing the sample to be strictly opposite to the sample. This is because the interval between the grating stripes is a physical constant and is always a constant value, and thus the correlation between the length in the image and the actual length can be determined by comparing the interval between the grating stripes with the width of the grating stripes in the image.

Embodiment 2 for Carrying Out the Invention (Testing Apparatus Suitable for Performing the Testing Method)

In performing the length measurement relating to the cross-sectional structure of the LSI device, such as the length measurement of a gate oxide film in the growth process thereof, the length measurement of a shallow trench isolation film in the growth process thereof, and the length measurement of a diffusion preventing film for preventing the diffusion of a metal from a metal wiring in the growth process thereof, for example, the following problem arises when the length measurement is immediately performed by the TEM apparatus.

Firstly, a sample needs to be produced to observe the cross-sectional structure, which produces a situation requiring an exposing process of exposing the cross-sectional structure by using an FIB apparatus or the like. This is also a situation in which a good result is not necessarily obtained from the sample, even if the sample is observed by the TEM apparatus. This is because electron scattering is affected by the size or thickness of the sample and is not easy to be adjusted. Therefore, a process of trial and error is repeated in the production of the sample until a good observation result is obtained. This causes a problem in that the process of trial and error involving switching between the FIB apparatus and the TEM apparatus takes time.

Accordingly, a measuring apparatus according to the embodiment example 2 to solve the above problem will be described. To describe the measuring apparatus according to the embodiment example 2, FIGS. 8, 9, and 10 will be used, wherein FIG. 8 illustrates the outline of the apparatus according to the embodiment example 2, FIG. 9 show a flowchart of the measurement performed by using the apparatus, and FIG. 10 illustrates a diaphragm used in the image clarification step of removing an unnecessary electron beam.

Figure 8:
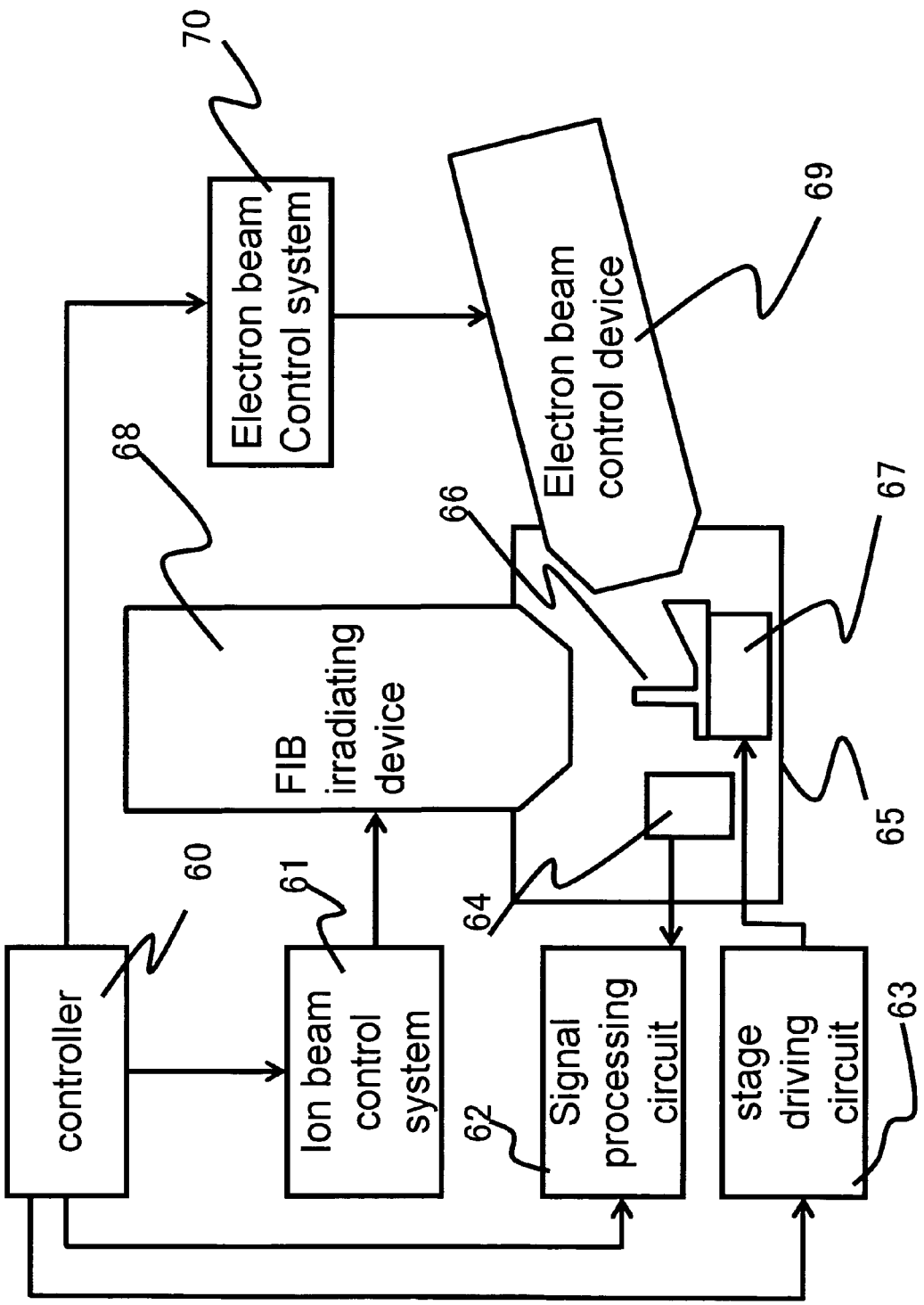
FIG. 8 is a diagram illustrating the outline of an apparatus according to the embodiment example 2.

Firstly, the apparatus according to the embodiment example 2 illustrated in FIG. 8 includes a controller 60, an ion beam control system 61, a signal processing circuit 62 for processing a signal output from an electron beam detector 64 and forming an electron beam diffraction image, a stage driving circuit 63, the electron beam detector 64 having a diaphragm which adjusts the amount of the electron beam and detecting an electron beam transmitted through a sample 66, a sample chamber 65 for maintaining a decompressed state to cause the FIB and the electron beam to directly advance with respect to the sample 66, a sample stage 67 on which the sample 66 is placed, an FIB irradiation device 68 for irradiating the FIB toward the sample 66, an electron beam irradiation device 69 for irradiating the electron beam toward the sample 66, and an electron beam control system 70.

The controller 60 includes an arithmetic and control circuit, such as a CPU, and sends commands to the ion beam control system 61 which controls the FIB irradiation device 68, the electron beam control system 70 which controls the electron beam irradiation device 69, the signal processing circuit 62, and the stage driving circuit 63 which drives the sample stage 67. As a result, the apparatus according to the embodiment example 2 operates following the flowchart shown in FIG. 9, and can perform the length measurement of the portion added by the manufacturing process.

Figure 9:
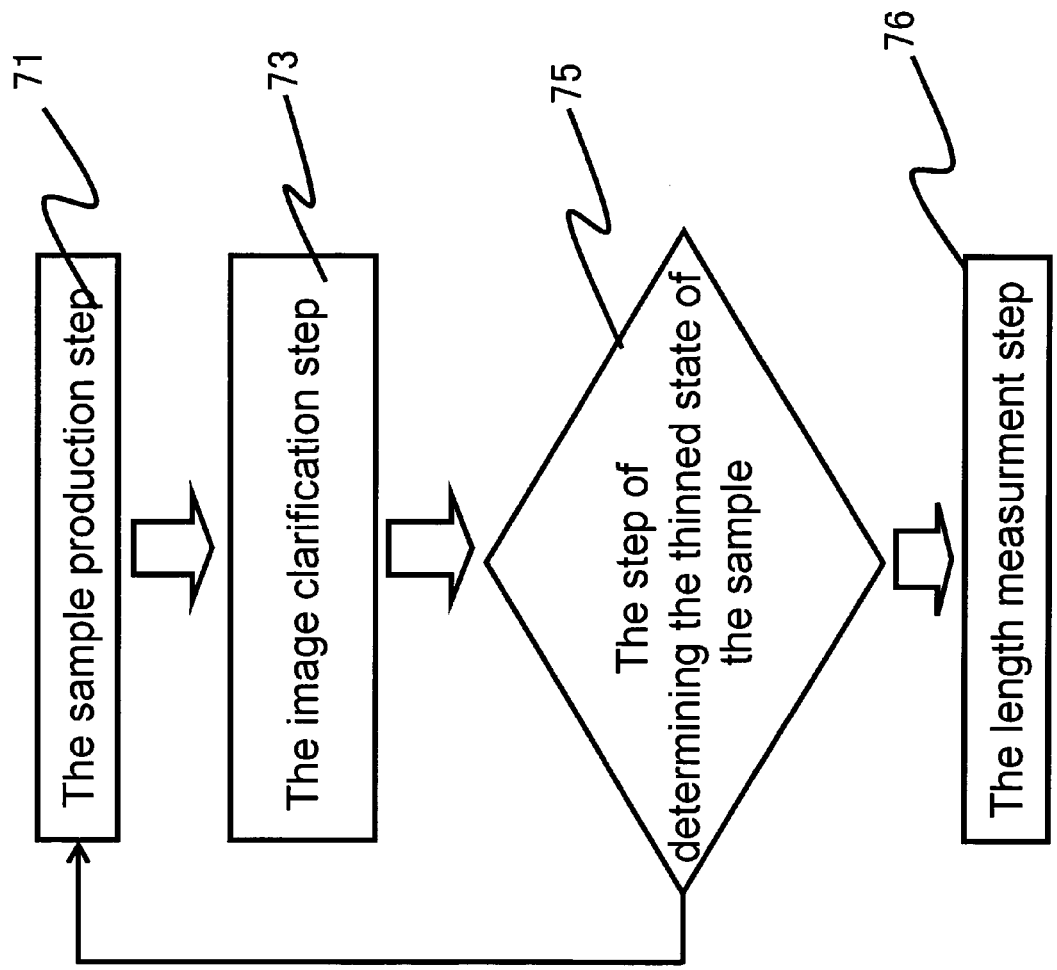
FIG. 9 is a diagram showing a flowchart for the apparatus according to the embodiment example 2 to perform the length measurement of the portion added by the manufacturing process.
Figure 10:
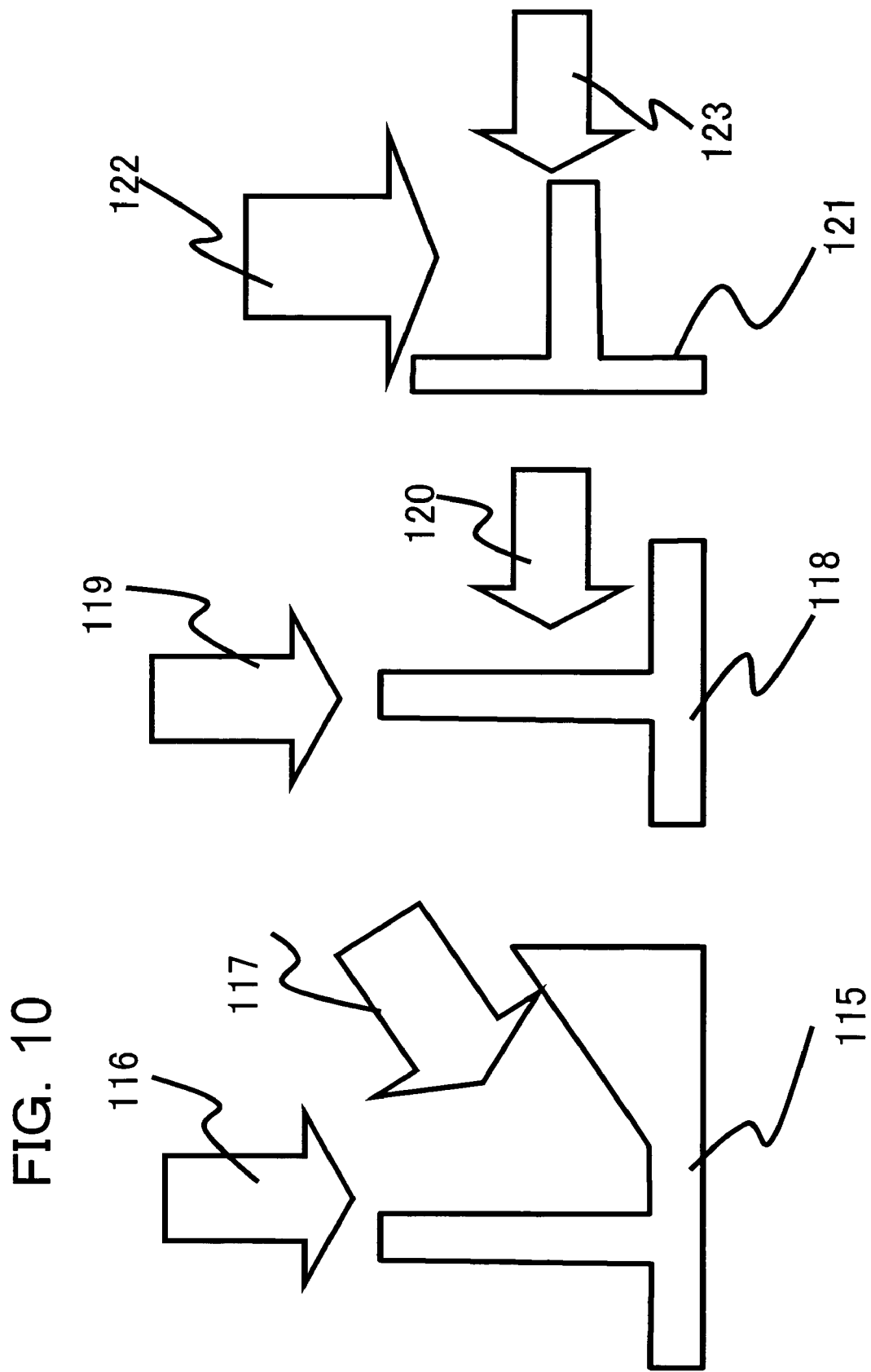
FIG. 10 is a diagram illustrating directions of the electron beam and directions of the FIB in a case in which three kinds of samples are different in shape.

Then, FIG. 9 shows the flowchart for the apparatus according to the embodiment example 2 to perform the length measurement of the portion added by the manufacturing process. Firstly, in a sample production step 71, the controller 60 sends a command to the stage driving circuit 63 to position the sample 66 on the sample stage 67. Further, via the ion beam control system 61, the controller 60 causes the FIB irradiation device 68 to irradiate the FIB from the above of the sample 66, to thereby thin the sample 66 and optimize the thickness of the sample 66. Then, in an image clarification step 73 of obtaining a clear electron diffraction image, the controller 60 first sends a command to the electron beam control system 70 to irradiate an electron beam to the sample 66 from the electron beam irradiation device 69.

The facing direction of the electron beam irradiation device 69 and the facing direction of the FIB irradiation device 68 are different from each other. This is because, while irradiation from the above is suitable for thinning the sample 66 by the irradiation of the FIB, irradiation of the electron beam from a lateral direction is suitable for observing a cross section of the sample 66 due to the transmission of the electron beam. However, the irradiation direction of the FIB and the irradiation direction of the electron beam do not need to be perpendicular to each other. This is because the irradiated electron beam is expected to transmit through the sample 66, and it suffices as long as the irradiation is performed from a direction not interfering with the FIB irradiation device.

The above will be described with reference to FIG. 10. FIG. 10 includes a left diagram, a center diagram, and a right diagram illustrating the shapes of three different kinds of samples.

Firstly, the left diagram illustrates the irradiation direction of the FIB and the radiation direction of the electron beam with respect to a sample 115 which includes a projecting portion and a slope portion used to observe a cross section. That is, to thin the projecting portion, the FIB is irradiated from the above, and the electron beam is radiated obliquely from the upper right along the slope portion.

The sample 115 is in the illustrated shape for the following reason. If the feature size of the sample 115 prior to the cutting out of the projecting portion is large as in the case of a semiconductor chip, the projecting portion for observing the cross section is formed at an edge of the semiconductor chip. However, it is time-consuming and difficult to trim the entirety of the semiconductor chip to be aligned with the lower part of the projecting portion. Thus, the slope portion has been provided in the direction of radiating the electron beam.

Secondly, the center diagram illustrates a case in which a sample 118 includes only the projecting portion facing upward, and the FIB is irradiated from the above while the electron beam is radiated from a side of the projecting portion. The sample 118 is in an upside-down T-shape, since the original feature size of the sample 118 is not so large, and thus the opposite ends of the sample 118 have been trimmed off by the irradiation of the FIB.

Further, the right diagram illustrates a case in which a sample 121 includes only the projecting portion facing the right direction, and the FIB is irradiated from the right side while the electron beam is radiated from the above. The sample 121 is in a laid-down T-shape, since the original feature size of the sample is not so large, and thus the upper and lower ends of the sample 121 have been trimmed off by the irradiation of the FIB.

Referring back to FIG. 9, the explanation of the image clarification step 73 of obtaining a clear electron diffraction image will be then continued. In the image clarification electron 73 of obtaining a clear electron diffraction image, the controller 60 sends a command to the signal processing circuit 62 to process a signal received by the electron beam detector 64 which detects the electron beam transmitted through the sample 66. Thereby, an electron beam diffraction image is formed.

Then, to adjust the amount of the electron beam transmitted through the sample for removing the diffracted electron beam, the controller 60 sends a command to the signal processing circuit 62 to adjust the size of the opening of the diaphragm included in the electron beam detector 64 for adjusting the amount of the electron beam. As a result, the electron beam diffracted by the crystal portion of the sample 66 is narrowed, and the shading of the image of the crystal portion becomes clear. Further, the diffraction grating stripes appearing in the crystal portion in the electron beam diffraction image are made clear.

Then, in a step 75 of determining the thinned state of the sample 66, a determination is made on whether the electron beam diffraction image obtained by adjusting the size of the opening of the diaphragm is sufficiently clear. If the electron beam diffraction image is determined not to be sufficiently clear, the amount of the thinning is specified in the controller 60 for commanding to return again to the sample production step 71. Meanwhile, if the electron beam diffraction image is determined to be sufficiently clear, the procedure advances to the next step.

The length measurement step 76 includes an operation of comparing the width of the grating stripes in the electron beam diffraction image formed by the crystal portion of the sample with the width of the portion added by the manufacturing process. Subsequent to the comparing operation, the actual thickness of the portion added by the manufacturing process is calculated from the grating constant of the crystal portion of the sample and from the ratio obtained from the above comparing operation between the width of the grating stripes and the width of the portion added by the manufacturing process.

Figure 11:
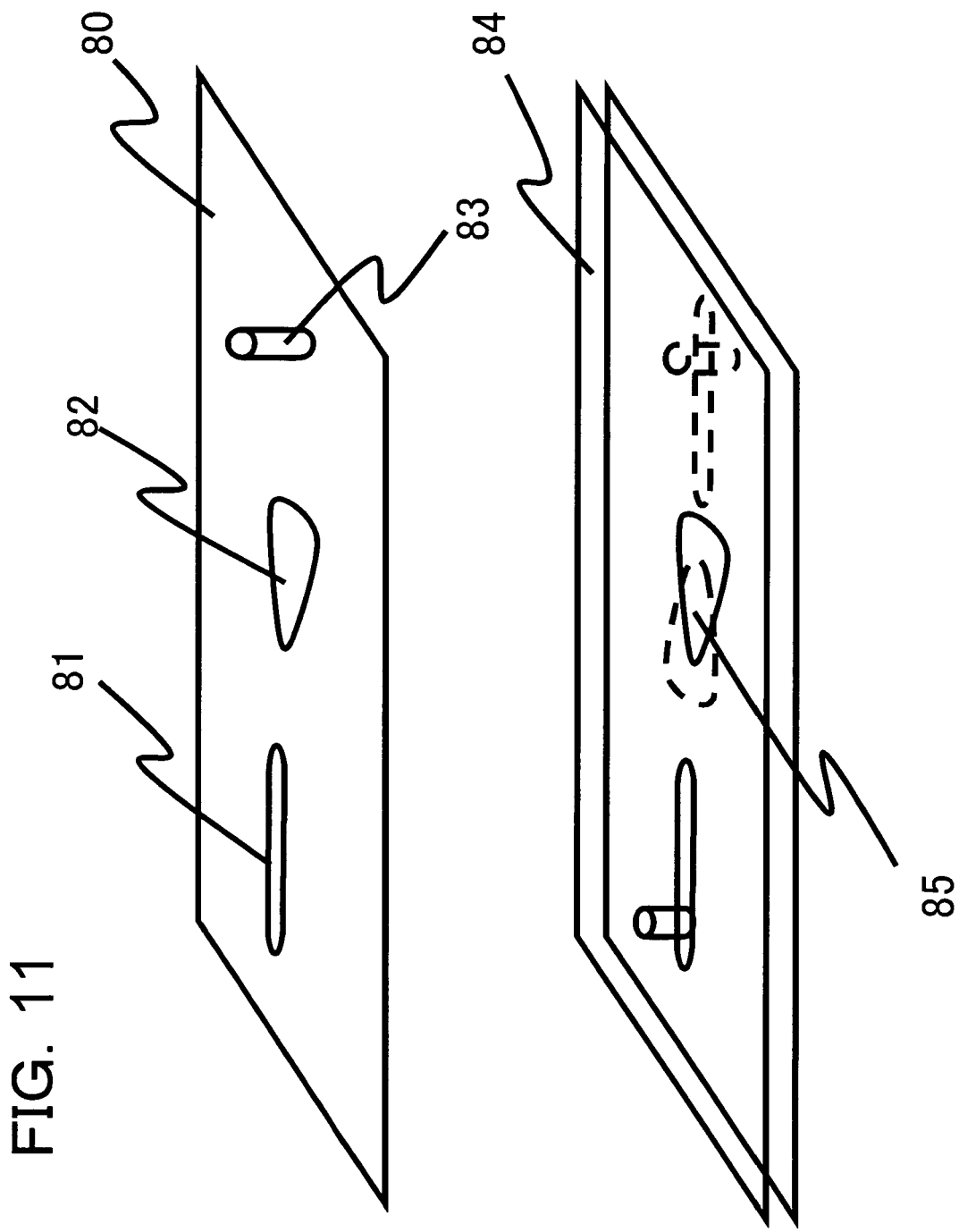
FIG. 11 is a diagram illustrating a diaphragm used in a diaphragm adjustment step aiming for the removal of the electron beam in the apparatus according to the embodiment example 2.

The above-described diaphragm included in the electron beam detector 64 is illustrated in FIG. 11. FIG. 11 includes an upper diagram illustrating a plate 80 which forms a diaphragm 84, and a lower diagram illustrating the entirety of the diaphragm 84.

That is, the diaphragm 84 illustrated in the lower diagram of FIG. 11 is formed by superimposing two plates 80 illustrated in the upper diagram of FIG. 11 in a face-to-face manner. The plate 80 includes a projection 83, a rectangular opening 81 having a constant width, and an opening 82 having a shape approximately the same as the cross section of an egg. An overlapped portion of the above-described openings 82, each having the shape approximately the same as the cross section of an egg, form an opening 85. The size of the above opening 85 can be adjusted by sliding one of the plates with respect to the other one of the plates. As long as the size of the opening 85 is changed by sliding the plate, the opening 82 does not necessarily have to be in the shape approximately the same as the cross section of an egg. Thus, the opening 82 may be in a spread-out shape (e.g., a fan shape) with a point of the opening serving as a starting point, or in an oval shape.

The opening 82 having the shape approximately the same as the cross section of an egg is formed into an oval cross-sectional shape for making the opening 85 into an approximately circular shape. Therefore, the shape approximately the same as the cross section of an egg is a figure obtained by superimposing a plurality of circles having gradually increased radii.

Figure 12:
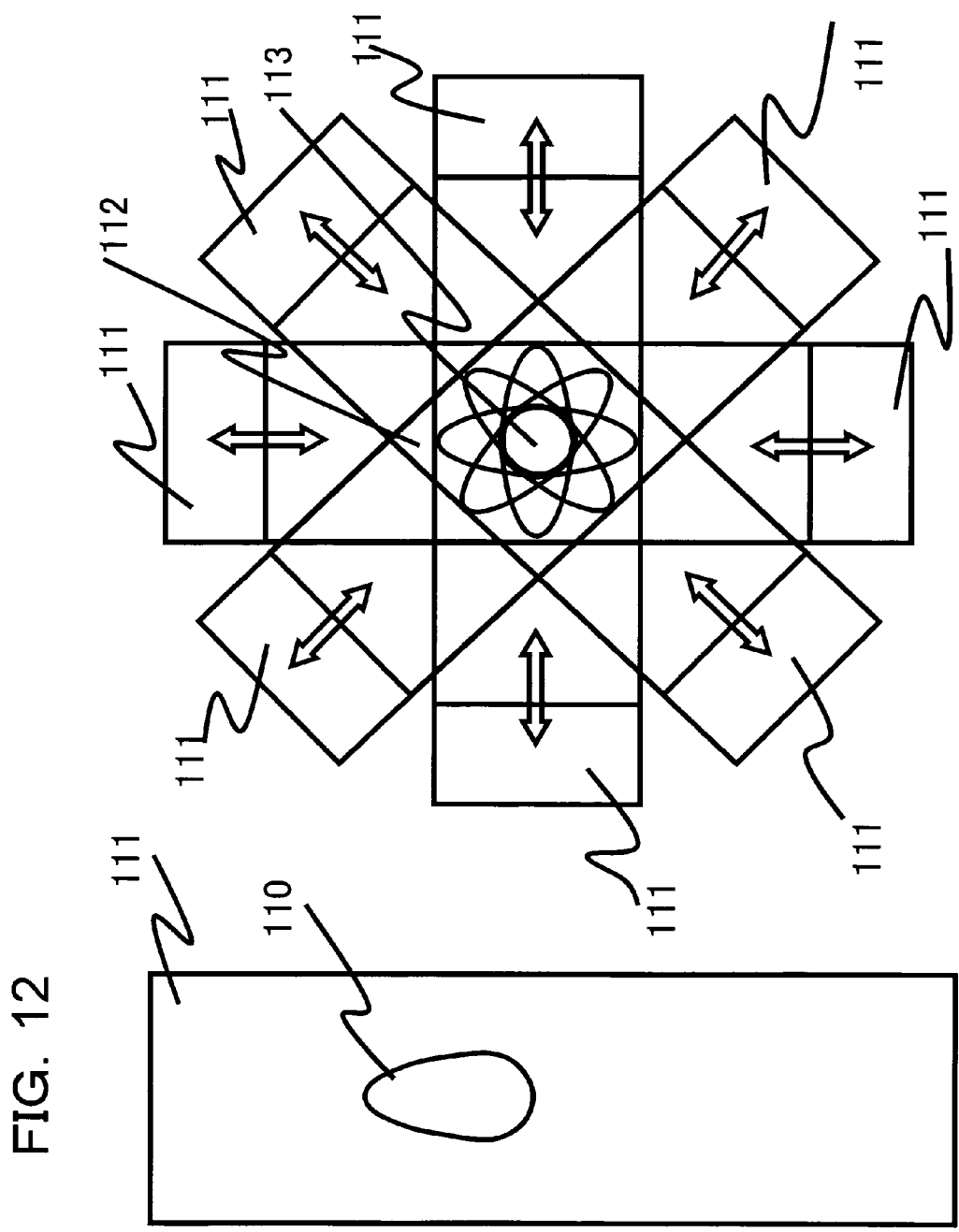
FIG. 12 is a diagram illustrating a modified example of the diaphragm.

Further, a modified example of the diaphragm is illustrated in FIG. 12. FIG. 12 includes a right diagram illustrating a diaphragm 112, and a left diagram illustrating a plate 111 forming the diaphragm 112. The plate 11 includes an opening 110 having a shape approximately the same as the cross section of an egg. The diaphragm 112 is formed by superimposing eight plates 111 such that one of the eight plates is disposed at an angle of 0 degree and thereafter the other plates are sequentially superimposed each with an angle of 45 degrees. Further, with the openings 110 of the respective plates overlapped with one another, an opening 113 is formed as a common portion of the openings 110. With this configuration, the size of the opening 113 can be continuously varied by sliding the respective plates 111 by the same amount at the same time. Thereby, the opening 113 is adjusted to an arbitrary size. The opening 110 is formed into the oval cross-sectional shape for making the opening 113 into an approximately circular shape. Therefore, the oval cross-sectional shape is actually the figure obtained by superimposing a plurality of circles having gradually increased radii, with the center positions of the circles slid little by little.

The above measuring apparatus according to the embodiment example 2 includes an FIB irradiation device for irradiating an FIB to a measured object from one angle, an electron beam irradiation device for irradiating an electron beam to the measured object from another angle, an electron beam detecting device for detecting the electron beam transmitted through the measured object, and an electron beam diaphragm provided between the electron beam detecting device and the measured object and capable of continuously adjusting the size of an opening through which the electron beam passes. According to the measuring apparatus of the embodiment example 2, the electron beam can be narrowed to an arbitrary amount by the above electron beam diaphragm.

Thus, the measuring method illustrated in the embodiment example 1 can be performed by the measuring apparatus according to the embodiment example 2. That is, the measuring apparatus according to the embodiment example 2 is the most suitable measuring apparatus for implementing the measuring method according to the embodiment example 1. Further, since the FIB irradiation device and the electron beam irradiation device are integrated, the result of observation by the TEM apparatus is obtained immediately after the production of the sample. Accordingly, there is an effect of reducing the trial and error period taken for the production of the sample.

Embodiment 3 for Carrying Out the Invention (Semiconductor Device Suitable for Performing the Testing Method)

In performing the length measurement relating to the cross-sectional structure of the LSI device, such as the length measurement of a gate oxide film in the growth process thereof, the length measurement of a shallow trench isolation film in the growth process thereof, and the length measurement of a diffusion preventing film for preventing the diffusion of a metal from a metal wiring in the growth process thereof, for example, the following problem arises when the length measurement is immediately performed by using a semiconductor device. That is, a sample needs to be produced to measure the cross-sectional structure, and the process of exposing the cross-sectional structure needs to be performed on an element portion of the semiconductor device. However, there is a problem in that it is troublesome to identify the element, which is the object of the processing.

Accordingly, a semiconductor device according to the embodiment example 3 to solve the above problem will be described. To describe the semiconductor device according to the embodiment example 3, FIGS. 13 and 14 will be used, wherein FIG. 13 illustrates the outline of the semiconductor device according to the embodiment example 3, and FIG. 14 illustrates a sample for the measurement produced by using the semiconductor device.

Figure 13:
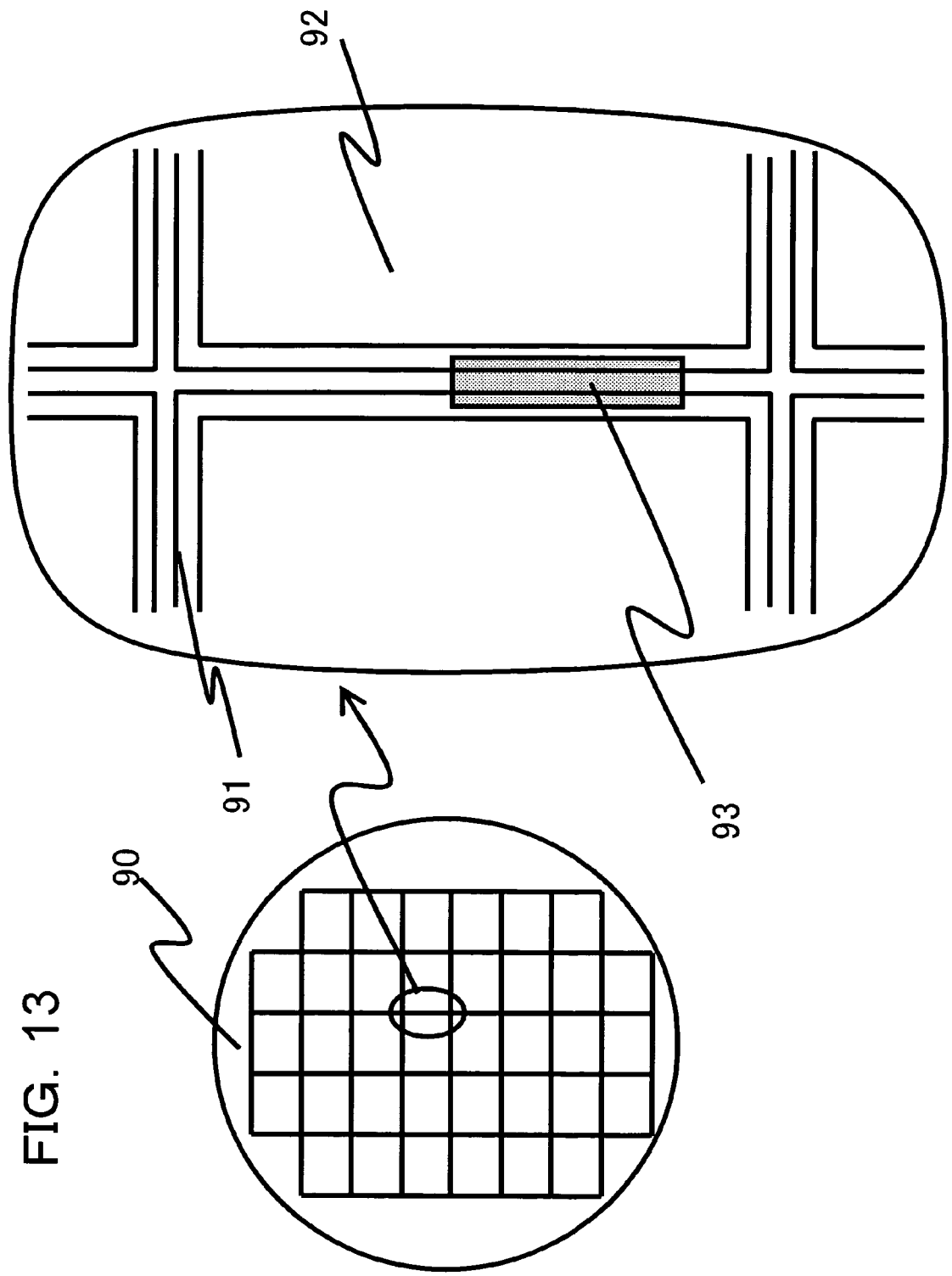
FIG. 13 is a diagram illustrating an edge of a semiconductor chip on a semiconductor substrate, and the location position of a monitor element.

Firstly, FIG. 13 includes a left diagram illustrating a semiconductor substrate 90, and a right diagram enlarging an edge of a semiconductor chip 92 on the semiconductor substrate. On the semiconductor substrate 90 illustrated in the left diagram of FIG. 13, the semiconductor chips 92 formed with circuit elements are manufactured in rows and columns. In the edge of the semiconductor chip 92 illustrated in the right diagram of FIG. 13, a scribe region is provided to cut the semiconductor chip 92 from the semiconductor substrate 90. Further, to prevent the semiconductor chip from being damaged, the scribe region is provided with a scribe line 91 for guiding a blade of a device which cuts the semiconductor chip 92 so that the blade will not swing from side to side. The scribe region is further provided with a monitor element 93 along the scribe line 91 at a position where the monitor element 93 is cut at the same time as the semiconductor chip 92 is cut.

In this case, the above monitor element 93 is the same in the cross-sectional structure as the circuit element on the semiconductor chip 92. Therefore, when the semiconductor chip 92 is cut into an individual piece, the FIB is irradiated in the apparatus according to the embodiment example 2 to process the above monitor element 93 into the shape illustrated in FIG. 14, and thereafter the electron beam is irradiated, so that an electron beam diffraction image reflecting the cross-sectional structure of the above monitor element 93 can be obtained.

Figure 14:
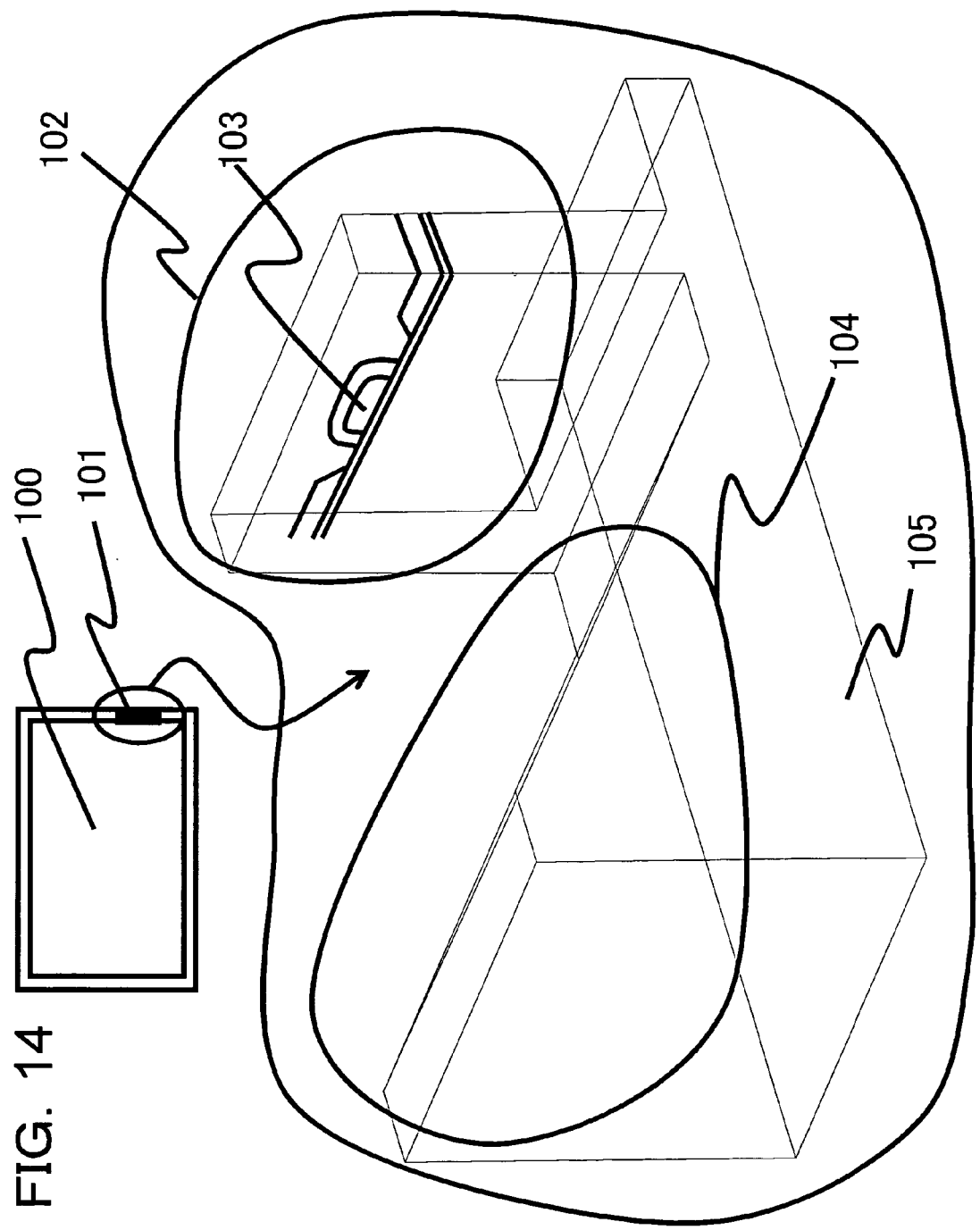
FIG. 14 is a diagram illustrating, in an upper diagram, the monitor element 101 of a semiconductor chip 100, and illustrating, in an enlarged diagram, a sample 105 processed by the irradiation of an FIB and carved out into a shape allowing the irradiation of an electron beam to an element cross section 103 of the monitor element 101.

A sample 105 illustrated in an enlarged diagram of FIG. 14 is obtained by processing, through the irradiation of the FIB, the monitor element 101 of a semiconductor chip 100 illustrated in an upper diagram of FIG. 14 to be carved out into a shape enabling the irradiation of the electron beam to an element cross section 103 of the monitor element 101. The above sample 105 includes, at an approximate distance of 100 µm to 200 µm from an edge of the semiconductor chip 100, a projecting portion 102 irradiated with an electron beam of a rectangular parallelepiped shape having an approximate thickness of 50 nm to 200 nm, and a slope portion 104 adjacent to the projecting portion 102 and having an angle of equal to or smaller than 45 degrees. The slope portion 104 is provided to enable the irradiation of the electron beam from the side of the slope portion 104 toward the projecting portion 102, to which the electron beam is irradiated.

The monitor element 101 may have the same cross section as that of the circuit element on the semiconductor chip 100 or may have the cross section of a part of the circuit element. Further, the monitor element 101 may have the shape of an insulation element which insulates between the circuit elements.

Figure 15:
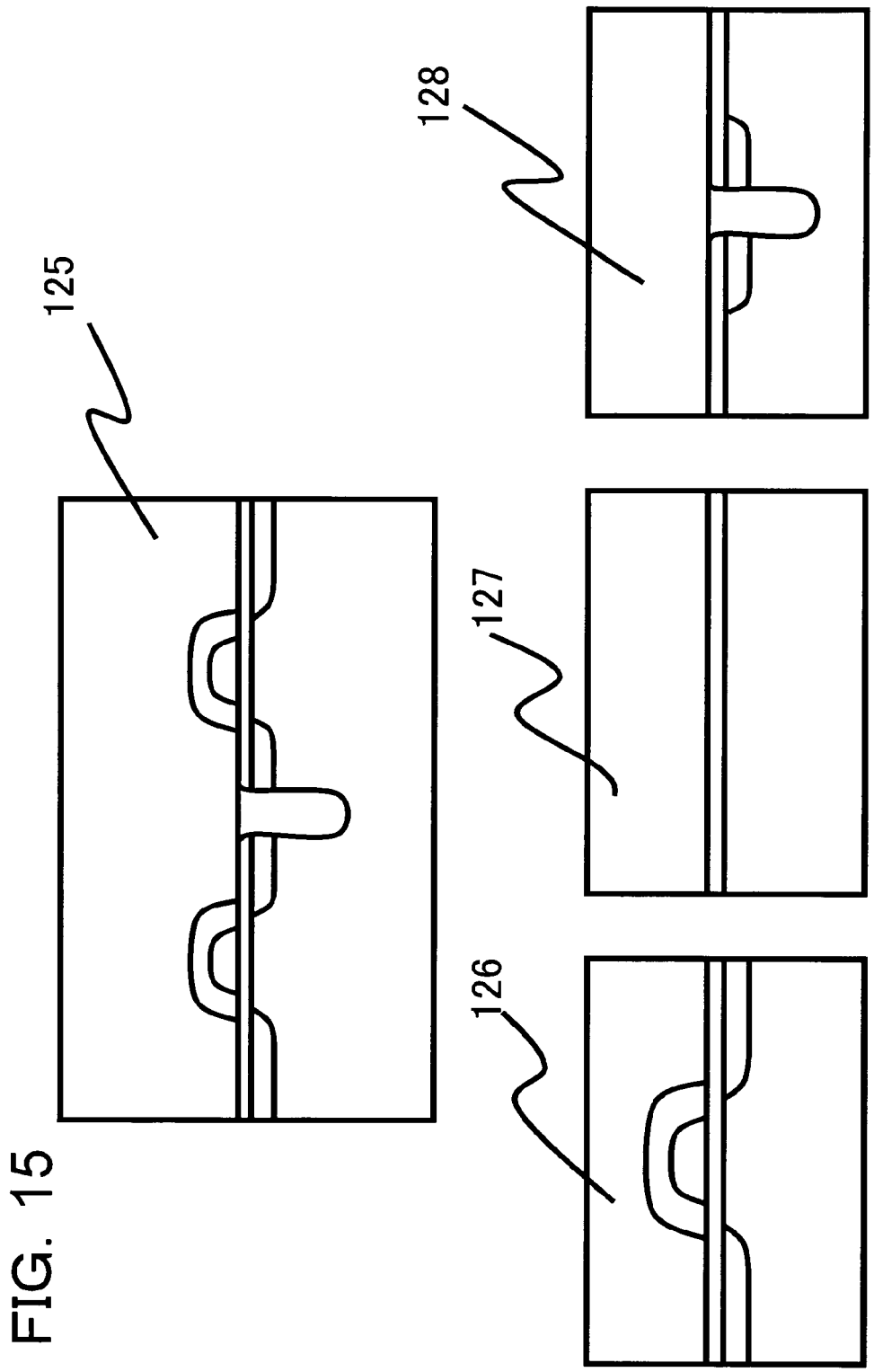
FIG. 15 is a diagram illustrating cross sections of a circuit element and cross sections of the monitor element.

The above will be described with reference to FIG. 15. FIG. 15 is a diagram illustrating cross sections of the circuit element and cross sections of the monitor element, and includes cross-sectional views 125 to 128. The cross-sectional view 125 illustrates a part of a cross section of an insulation element which electrically separates MOS transistors forming the circuit elements. Further, the cross section view 126 illustrates a monitor element having the same cross-sectional structure as that of the MOS transistor forming the circuit element. Furthermore, the cross section view 127 illustrates a monitor element having a cross-sectional structure in which only a gate oxide film portion of the MOS transistor forming the circuit element is extracted. Still further, the cross-sectional view 128 illustrates a monitor element having a cross-sectional structure in which the insulation element for separating the MOS transistors is extracted.

To briefly summarize the above, the semiconductor device according to the embodiment example 3 is a semiconductor device including a circuit element forming a semiconductor circuit, a measurement element used in a measurement, and a cutting region for cutting into an individual piece. The semiconductor device is characterized by being formed on a semiconductor substrate, and is cauterized in that the circuit element and the measurement element are the same in the cross-sectional structure, that the measurement element is provided in the cutting region at a position where the measurement element is cut when the semiconductor device is cut into the individual piece from the semiconductor substrate, and that a cut surface of the measurement element is used in the measurement.

In the semiconductor device according to the embodiment example 3, the cross section of the above measurement element is observable, when the semiconductor device is cut apart. Accordingly, the measuring method of the embodiment example 1 can be easily performed on the measurement element. Further, the measurement element and the actual circuit element in the semiconductor device are entirely or partially the same in structure. Thus, there is an effect of enabling the length measurement of the structure of the measurement element similar to the structure of the circuit element, without destroying the actual circuit element. Furthermore, since the measurement element is located at an edge of the semiconductor device, there is an effect of enabling easy length measurement by the measuring method of the embodiment example 1 using the measuring apparatus of the embodiment example 2.

REFERENCE NUMERALS 1 semiconductor detector
2 fixing pin
3 guide hole
4 lever pin
5 rotary ring
6 board
7 shaft
10 sample
11 electron lens
12 electron diffraction image
13 unscattered transmitted electron beam
14 scattered electron beam
15 crystal portion
16 image corresponding to crystal portion of sample
17 diaphragm
20 sample production step
22 image clarification step of obtaining clear electron diffraction image
24 length measurement step
30 semiconductor chip
31 observed object
32 FIB
33 sample
34 crystal substrate
35 portion added by manufacturing process
40 sample
41 electron lens
42 electron diffraction image
43 hardly-diffracted transmitted electron beam
44 diffracted transmitted electron beam
45 crystal portion
46 image of crystal portion
47 diaphragm
50 portion added by manufacturing process
51 interlayer insulation film
52 image of crystal portion
53 solid line
54 white arrow
60 controller
61 ion beam control system
62 signal processing circuit
63 stage driving circuit
64 electron beam detector
65 sample chamber
66 sample
67 sample stage
68 FIB irradiation device
69 electron beam irradiation device
70 electron beam control system
71 sample production step
73 image clarification step of obtaining clear electron diffraction image
75 step of determining thinned state
76 length measurement step
80 plate
81 rectangular opening
82 opening having shape approximately the same as cross section of egg
84 diaphragm
85 opening
90 semiconductor substrate
91 scribe line
92 semiconductor chip
93 monitor element
100 semiconductor chip
101 monitor element
102 portion irradiated with electron beam
103 element cross section
104 slope portion
105 sample
110 opening
111 plate
112 diaphragm
113 opening
115, 118, 121 sample
116, 119, 123 FIB
117, 120, 122 electron beam
125, 126, 127, 128 cross-sectional view
130 upper diaphragm plate
131 upper retaining mechanism
132 upper diaphragm hole
133 lower diaphragm plate
134 lower retaining mechanism
135 electron beam
136 lower diaphragm hole

What is claimed is:

1. A measuring method comprising:
a step of producing a sample by thinning an object including a crystal portion;
a step of irradiating an electron beam to the sample and narrowing, to an arbitrary amount, an electron beam which is included in a transmitted electron beam transmitted through the sample and which is diffracted by the crystal portion, to thereby obtain electron beam imaging from the transmitted electron beam; and
a step of comparing, in the electron beam imaging, the width of grating stripes obtained from the crystal portion with the width of an arbitrary portion.

2. The measuring method described in claim 1,
wherein, in the step of producing the sample,
the object including the crystal portion is thinned by irradiation of an FIB.

3. The measuring method described in claim 1,
characterized in that, in the step of obtaining the electron beam imaging,
the step is performed by using a device which detects the electron beam, and
that a diaphragm provided between the sample and the device which detects the electron beam is made continuously variable,
to thereby narrow, to the arbitrary amount, the electron beam diffracted by the crystal portion.

4. The measuring method described in claim 1,
characterized in that, in the step of comparing, in the electron beam imaging, the width of grating stripes obtained from the crystal portion with the width of an arbitrary portion,
the ratio between the width of the grating stripes and the width of the arbitrary portion in the electron beam imaging is further obtained, and
that the actual width of the arbitrary portion is obtained from a grating constant corresponding to the actual grating stripes and from the ratio.

5. A measuring apparatus comprising:
an FIB irradiation device for irradiating an FIB to a measured object from one angle;
an electron beam irradiation device for irradiating an electron beam to the measured object from another angle;

an electron beam detecting device for detecting the electron beam transmitted through the measured object; and an electron beam diaphragm provided between the electron beam detecting device and the measured object and capable of adjusting an opening through which the electron beam passes;

characterized in that the diaphragm is formed by disposing eight rectangular plates each including a first opening at a central portion thereof such that one rectangular plate of the eight rectangular plates is disposed at an angle of 0 degree and the other rectangular plates are sequentially superimposed each with an angle of 45 degrees, with the first openings partially overlapped with one another, and that the eight rectangular plates are slid by an equal amount along the respective disposition angles thereof with respect to a second opening formed by a common portion of the first openings of the eight rectangular plates, to thereby adjust the size of the second opening.

6. A measuring apparatus comprising:

an FIB irradiation device for irradiating an FIB to a measured object from a horizontal direction;

an electron beam irradiation device for irradiating an electron beam to the measured object from a vertical direction;

an electron beam detecting device for detecting the electron beam transmitted through the measured object; and an electron beam diaphragm provided between the electron beam detecting device and the measured object and capable of adjusting an opening through which the electron beam passes;

wherein that the diaphragm is formed by disposing eight rectangular plates each including a first opening at a central portion thereof such that one rectangular plate of the eight rectangular plates is disposed at an angle of 0 degree and the other rectangular plates are sequentially superimposed each with an angle of 45 degrees, with the first openings partially overlapped with one another, and wherein the eight rectangular plates are slid by an equal amount along the respective disposition angles thereof with respect to a second opening formed by a common portion of the first openings of the eight rectangular plates, to thereby adjust the size of the second opening.

* * * * *